(12) United States Patent
Bastiaansen (10) Patent No.: US 10,578,695 B2
(45) Date of Patent: Mar. 3, 2020

(54) DIFFERENTIATED TISSUE EXCITATION IN MRI

(71) Applicant: Centre Hospitalier Universitaire Vaudois, Lausanne (CH)

(72) Inventor: Josefina Adriana Maria Bastiaansen, Lausanne (CH)

(73) Assignee: Centre Hospitalier Universitaire Vaudois, Lausanne (CH)

( * ) Notice: Subject to any disclaimer, the term of this patent is extended or adjusted under 35 U.S.C. 154(b) by 480 days.

(21) Appl. No.: 15/487,542

(22) Filed: Apr. 14, 2017

(65) Prior Publication Data

US 2017/0299678 A1 Oct. 19, 2017

(30) Foreign Application Priority Data

Apr. 18, 2016 (EP) .................... 16165763

(51) Int. Cl.
| | |
|---|---|
| *G01R 33/48* | (2006.01) |
| *A61B 5/055* | (2006.01) |
| *A61B 5/00* | (2006.01) |
| *G01R 33/385* | (2006.01) |

(52) U.S. Cl.
CPC .......... *G01R 33/4828* (2013.01); *A61B 5/055* (2013.01); *A61B 5/4872* (2013.01); *G01R 33/385* (2013.01)

(58) Field of Classification Search
CPC .... A61B 5/055; A61B 5/4872; G01R 33/385; G01R 33/4828; G01R 33/485; G01R 33/543; G01R 33/5607; G01R 33/561
See application file for complete search history.

(56) References Cited

U.S. PATENT DOCUMENTS

| | | | |
|---|---|---|---|
| 5,510,713 | A | 4/1996 | Bernstein |
| 5,557,202 | A | 9/1996 | Miyazaki et al. |
| 5,856,744 | A | 1/1999 | Block et al. |
| 8,248,070 | B1 | 8/2012 | Wheaton |

(Continued)

FOREIGN PATENT DOCUMENTS

| | | |
|---|---|---|
| EP | 1059540 A2 | 12/2000 |
| EP | 2390677 | 11/2011 |

(Continued)

OTHER PUBLICATIONS

Deligianni et al: "Water-selective excitation of short T2 species with binomial pulses", Magnetic Resonance in Medicine, vol. 72, No. 3, Oct. 7, 2013 (Oct. 7, 2013), pp. 800-805, XP055307472.

(Continued)

*Primary Examiner* — Michael T Rozanski
(74) *Attorney, Agent, or Firm* — Woodard, Emhardt, Henry, Reeves & Wagner, LLP (57) ABSTRACT

Selectively exciting bulk protons in certain tissue components, e.g. water, while suppressing the excitation of others, e.g. fat, can lead to images with better contrast for desired features. The invention provides binomial, off-resonance RF excitation pulses for differentiating tissue excitation that yields a larger fat suppression that prior art water excitation methods. Proper balancing of the frequency offset and the pulse duration with a relative phase offset between the pulses leads to large-bandwidth pass- and stopbands for water and fat, respectively. The pulses can be applied with short, or even zero, interpulse delay, leading to substantial time savings in the imaging sequence.

12 Claims, 7 Drawing Sheets

(56) References Cited

U.S. PATENT DOCUMENTS

| | | |
|---|---|---|
| 2005/0122105 A1 | 6/2005 | Avram et al. |
| 2007/0052415 A1 | 3/2007 | Asano |
| 2009/0143666 A1 | 6/2009 | Edelman et al. |
| 2009/0256563 A1 | 10/2009 | Lee et al. |
| 2010/0052675 A1 | 3/2010 | Priatna et al. |
| 2010/0198046 A1 | 8/2010 | Takei |
| 2011/0267057 A1 | 11/2011 | He et al. |
| 2012/0194193 A1 | 8/2012 | Rehwald et al. |
| 2013/0088226 A1 | 4/2013 | Miyazaki |
| 2013/0113486 A1 | 5/2013 | Imamura et al. |
| 2014/0100443 A1 | 4/2014 | Koldzoglou |
| 2014/0300538 A1 | 10/2014 | Rijnders |

FOREIGN PATENT DOCUMENTS

| | | |
|---|---|---|
| JP | 2004000749 | 7/2005 |
| JP | 2006000478 | 7/2007 |
| JP | 2008000626 | 6/2008 |
| JP | 2009034152 | 2/2009 |
| JP | 2009028398 | 8/2010 |
| JP | 2013027461 | 7/2013 |
| WO | WO 1999/015915 | 4/1999 |
| WO | WO 2009/136131 | 11/2009 |
| WO | WO 2011/015865 | 2/2011 |
| WO | WO 20131082677 | 6/2013 |
| WO | WO 20131102683 | 7/2013 |
| WO | WO 2015/086476 | 6/2015 |
| WO | WO 2015/102169 | 7/2015 |

OTHER PUBLICATIONS

Hardy P A el Al: "Fat suppressed MRI of Articular Cartilage with a spatial-spectral excitation pulse", Journal of Magnetic Resonce Imaging, Society for Magnetic Resonance Imaging, Oak Brook, IL, US, vol. 8, No. 6, Nov. 1, 1998 (Nov. 1, 1998), pp. 1279-1287, XP008040958.

Lin Hung-Yu et al: "Rapid phase-modulated water excitation steady-state free precession for fat suppressed cine cardiovascular MR", Journal of Cardiovascular Magnetic Resonance, Biomed Central Ltd, London UK, vol. 10, No. 1, May 13, 2008 (May 13, 2008), p. 22, XP021037708.

Morrell. Rapid Fat Suppression in MRS of the Breast with Short Binomial Pulses, Journal of Magnetic Resonance Imaging 24:1172-1176 (2006).

Ye el al: "Robust Selective Signal Suppression Using Binomial Off-Resonant Rectangular (BORR) Pulses" Journal of Magnetic Resonance Imaging 39:195-202 (2014).

Ye et al. (2015). Retrobulbar magnetic resonance angiography using binomial off-resonant rectangular (BORR) pulse. Magnetic Resonance in Medicine, 74(4), 1050-1055 (2015) doi: 10.1002/mrm25498.

Fig. 10

DIFFERENTIATED TISSUE EXCITATION IN MRI

CROSS-REFERENCE TO RELATED APPLICATION

This application claims the foreign priority benefit of European Patent Application No. 16165763.0, filed Apr. 18, 2016, which is hereby incorporated by reference.

FIELD OF THE INVENTION

The present invention relates to magnetic resonance imaging (MRI), in particular to RF excitation pulses aimed at differentiated tissue excitation during MRI recording.

BACKGROUND OF THE INVENTION

The suppression of fat signals is an important component of many MRI exams in the clinic. Signals from fat that resonate at different frequencies compared with water need to be suppressed to obtain high quality images. The prevalence of chemical shift artifacts become higher with increasing magnetic field strengths and the suppression of fat resonances becomes increasingly complicated.

Techniques aimed at suppressing fat take advantage of the two characteristic differences in the behavior of water and fat, either the difference in relaxation times or chemical shift effects. In general, approaches that are used to achieve fat signal suppression consist of the application of pre-pulses, so called fat saturation (FS) or inversion recovery (IR) pulses, that result in nulling of the fat signals prior to the MRI imaging sequence, or by the use of specific radiofrequency (RF) excitation pulses that are water selective, such as in the case of binomial 1-1 RF excitation pulse schemes, the so-called water selective water excitation (WE). In general these methods are sensitive to magnetic field inhomogeneities, imperfect RF saturation or inversion pulses, or limited by the magnetization recovery time (T1) of the fat protons.

The following papers explore selective signal suppression using two consecutive binomial off-resonant rectangular (BORR) pulses with a phase difference of $\pi$. Ye et al. (2014). Robust selective signal suppression using binomial off-resonant rectangular (BORR) pulses. *Journal of Magnetic Resonance Imaging*, 39(1), 195-202. doi: 10.1002/jmri.24149 and Ye et al. (2015). Retrobulbar magnetic resonance angiography using binomial off-resonant rectangular (BORR) pulse. *Magn Reson Med*, 74(4), 1050-1056. doi: 10.1002/mrm.25498. The results presented herein will be discussed in more detail later.

Hence, an improved method for reducing MR signals originating from fat in MR imaging would be advantageous, and in particular a method that is less sensitive to magnetic field inhomogeneities would be advantageous.

OBJECT OF THE INVENTION

It is an object of the present invention to provide a new type of binomial RF excitation pulse that specifically excites the water protons and efficiently suppresses lipid signals, and solves the above mentioned problems of the prior art.

The selective excitation of water and simultaneous suppression of fat is a well known objective since these are dominant tissue components in humans. Similar objectives where one tissue component is to be excited and another suppressed in order to get a desired image are sometimes relevant.

It is therefore a further object to provide a new type of generalized binomial RF excitation pulses that specifically excites bulk protons in one tissue component and efficiently suppresses bulk protons in another tissue component.

SUMMARY OF THE INVENTION

Thus, the above described object and several other objects are intended to be obtained in a first aspect of the invention by providing a method for differentiating tissue excitation in magnetic resonance imaging (MRI), comprising applying during an image acquisition sequence of an MRI system first and second radio-frequency (RF) excitation pulses, where the first and second pulses are off-resonance to protons in a tissue component to be excited by having a central frequency, f, offset from a central resonance frequency of protons in the tissue component to be excited, $f_e$, by a predetermined frequency offset, $\Delta f$, in a direction away from a central resonance frequency of protons in a tissue component to be suppressed, $f_s$, where the first and second pulses have the same RF excitation angle, $\alpha$, and respective phases, $\varphi_1$ and $\varphi_2$, characterized in that a phase shift between the pulses is related to the frequency offset, $\Delta f$, and a pulse duration of the first pulse, $\tau_1$, by:

$$\varphi_1 = \varphi_0;\ \varphi_2 = \varphi_0 + r 2\pi \Delta f \tau_1$$

with r being a number in the interval [0.9; 1.1], resulting in a pulse sequence having a passband including $f_e$ in a frequency response profile for protons in the tissue component to be excited and a stopband including $f_s$ in a frequency response profile for protons in the tissue component to be suppressed.

In the following, a number of further aspects and preferred and/or optional features and elements will be described in relation to various embodiments of the invention. Features or elements described in relation to one embodiment or aspect may be combined with or applied to the other embodiments or aspects where applicable.

The resonance frequencies $f_e$ and $f_s$ depends on the magnetic field strength $B_0$, and thus the values selected for f and $\Delta f$ will typically also be different for different $B_0$. Prior art conventional water excitation methods using for example two binomial RF pulses are normally described by a model where a fat and a water proton are at equilibrium, with their magnetization vectors both pointing along the z-axis in the direction of the main magnetic field $B_0$. The first pulse causes both vectors be tipped partially toward the transverse plane and begin to precess. Because fat and water protons precess at different frequencies, they will be exactly 180° out of phase after a few microseconds, more exactly after $t=1/(2\ \delta B_0 \gamma)$. At this time the second pulse will rotate the fat vector back to its original position along the z-axis while rotating the water vector further towards the transverse plane.

Although the present invention also applies two binomial RF pulses, there are important differences and the model above cannot be applied, let alone that the interpulse delay can be shorter than a 90° dephasing of the protons. Thus, in a preferred embodiment any interpulse delay, t, between the end of the first pulse and the beginning of the second pulse is smaller than a time for 90° phase evolution between protons in the respective tissue components:

$$t \leq 1/(4\ \delta B_0 \gamma),$$

where δ is the chemical shift between protons in tissue to be excited and suppressed, $\delta=(f_s-f_e)/f_e$, $B_0$ is the magnetic field strength, and γ is the gyromagnetic ratio of the nucleus.

In another preferred embodiment, the interpulse delay is shorter than $1/(8\,\delta\,B_0\gamma)$ such as shorter than $1/(12\,\delta\,B_0\gamma)$, or shorter than 200 μs, such as shorter than 100 μs, preferably shorter than 50 μs, 25 μs or 10 μs. In a preferred embodiment, the interpulse delay is as short as possible, typically limited by the electronic components and the RF antennas of the MRI system. The shorter the interpulse delay, the shorter is the overall duration of the excitation pulse sequence, which again leads to shorter imaging sequences and more efficient use of MRI scanner time and shorter scanning times for subjects.

For very short and zero interpulse delays, the first and second pulses may overlap and effectively be first and second parts of a single, phase-modulated pulse or be expressed as a superposition of different pulses. In these cases, the pulse duration of the first pulse will be the time until the phase modulation. For the sake of simplicity, they will be referred to as first and second pulses without this being interpreted as limiting the scope to exclude the cases of very short or zero interpulse delays.

The interaction between protons and RF pulses depends on many parameters (or settings) of the individual RF pulses, such as the RF pulse shape, duration, frequency off-set, amplitude, and phase modulation, as well as on relative parameters such as interpulse delay and relative phase off-set. Also, since the combined excitation-suppression is a two-pulse-process, the resulting pass- and stopbands cannot be seen in the frequency spectra of the pulses nor in the (single pulse) absorption spectra of the protons. At present, there is no clear model for the interaction between the protons and the RF pulses of the present invention, and the first and second pulses are best described by their frequency response profiles (FRP) for bulk protons in the tissue components to be excited and suppressed, respectively. Such FRPs are typically obtained by numerical simulation, and the resulting FRPs may be used to select applicable parameters for the first and second pulses, thus providing a 'recipe' for implementing the invention. It should be noted that any numerical simulation approach may be used to simulate the magnetization and generate FRPs. Therefore, in a preferred embodiment of the invention, the method further comprises selecting a value of at least one of the following parameters: pulse shape, pulse amplitude, Δf, $\tau_1$, α, $\varphi_0$, $f_e$, $f_s$, $B_0$, or t, by performing a numerical simulation of the excitation and suppression of bulk protons in the tissue components with at least the parameter for which a value is to be selected as a variable; and selecting a value of the parameter from the result of the simulation under an objective of the differentiated tissue excitation. Objectives of the excitation pulse sequence can be one or more of the following statements:

- large excitation of protons in tissue component to be excited
- large passband bandwidth (low Δf-sensitivity of excitation)
- large suppression of protons in tissue component to be suppressed
- large stopband bandwidth (low Δf-sensitivity of suppression)
- low sensitivity to main magnetic field inhomogeneities ($B_0$)
- low sensitivity to RF field inhomogeneities ($B_1$)

The phase offset of at least substantially $2\pi\,\Delta f\,\tau_1$ of the second pulse relative to the first pulse, together with the constraints of the pulses having the same Δf and the same RF excitation angle, are important pulse design parameters. It is this balancing of the frequency offset and the pulse duration with a relative phase offset between the pulses that leads to the large-bandwidth pass- and stopbands. This means, that it is not sufficient for a prior art excitation pulse pair to accidentally have the same relative phase offset, Δφ, as that of first and second pulses according to the invention, if Δf and $\tau_1$ of the first pulse in the pair are not related to the relative phase offset via $\Delta\varphi=2\pi\,\Delta f\,\tau_1$. On the other hand, it can be seen from numerical simulations (not shown) that smaller deviations from this relation still give usable results, for which reason the factor r in the interval [0.9; 1.1] is multiplied to allow for deviations of up to 10%. In a preferred embodiment, r is in the interval [0.95; 1.05], such as in the interval [0.97; 1.03].

Figure 3A:
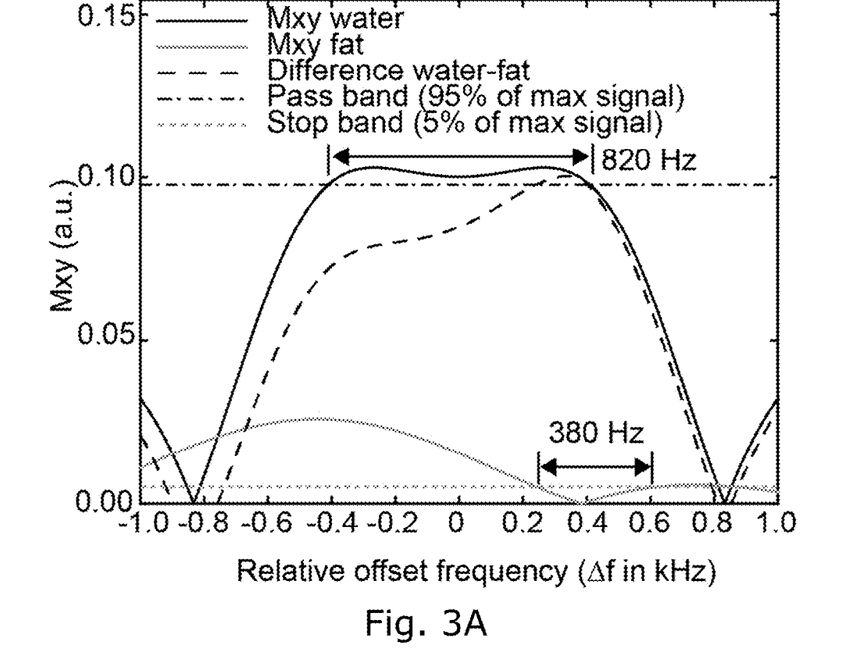
FIGS. 3A and 3B show numerical simulations of the magnetization as function of the frequency, a frequency response profile (FRP) of an embodiment of the invention (FIG. 3A, LIBRE) and of a prior art implementation of a binomial pulse (FIG. 3B, Ye et al. (2014)).

That the pulse sequence has a passband including $f_e$ in a FRP for protons in the tissue component to be excited means that this FRP has a peak of high amplitude covering a frequency range that includes $f_e$. In a preferred embodiment, the passband has an amplitude over 95% of maximum amplitude over a range of at least 200 Hz. Similarly, that the pulse sequence has a stopband including $f_s$ in a FRP for protons in the tissue component to be suppressed means that this FRP has a trough of low amplitude covering a frequency range that includes $f_s$. In a preferred embodiment, the stopband has an amplitude under 5% of the maximum amplitude over a range of at least 200 Hz. The bandwidth of the pass- and stopband is important for the robustness towards magnetic field inhomogeneities. Examples of a passband and a stopband for the water-fat scenario are shown in FIG. 3A.

It is also preferred that the first and second pulses have the same pulse duration $\tau_2=\tau_1$. Since the RF excitation angle, α, is defined by the pulse duration times the amplitude, $\alpha=B_1*\tau$, the constraints of the pulses having the same RF excitation angle and duration, implies that they will also have the same amplitude. These preferred parameters leads to a simpler pulse design and more efficient excitation and/or suppression.

In a preferred embodiment, the first and second RF pulses have a shape in the time domain that gives rise to a sinc-like frequency response. Thus, it is preferred that the first and second RF pulses have a rectangular pulse shape, or alternatively a triangular or half-circular pulse shape, in the time domain. For such pulse shapes, the pulse duration will affect the points of zero-crossings of the sinc in the frequency response profile, and thus influence the position of the stopband. For this purpose, In a preferred embodiment, each of the first and the second pulse is has a duration, $\tau_{1,2}$, in the interval 0.6-0.9 ms. In another preferred embodiment, a total pulse duration of the first and second pulses, $\tau=\tau_1+\tau_2$, is in the interval 1.2-1.8 ms, here the first and second pulses may have the same or different durations.

The invention is particularly, but not exclusively, advantageous for obtaining:

- Broad suppression bandwidth resulting in enhanced efficiency of lipid signal suppression.
- Significantly reducing the bright fat signals in MRI.
- Robust to magnetic field inhomogeneities.
- Low specific absorption rate (SAR).
- Provides near complete fat suppression in large volumes.
- Complete fat suppression even in 3D radial imaging.
- Shorter interpulse delay and thus shorter overall sequence duration In a preferred embodiment, the method is directed at water excitation and fat suppression, meaning that a dominating nuclear magnetic resonance (NMR) signal from a tissue component to be excited is from water and dominating NMR signal from a tissue component to be suppressed is from fat. This implies the following values:

| Water - fat | $B_0 = 1.5T$ | $B_0 = 3T$ | $B_0 = 7T$ |
|---|---|---|---|
| $f_e$ | 0 Hz | 0 Hz | 0 Hz |
| $f_s$ | −220 Hz | −440 Hz | −1030 Hz |
| $\delta$ | 3.1 ppm | 3.1 ppm | 3.1 ppm |
| $t = 1/(4 \delta B_0 \gamma)$ | 1.1 ms | 0.6 ms | 0.2 ms |

In a second aspect, the invention relates to the use of this embodiment of the method of the first aspect to reduce MR signals originating from fat in an MR image.

In another preferred embodiment, the method is directed at fat excitation and water suppression, meaning that a dominating nuclear magnetic resonance (NMR) signal from a tissue component to be excited is from fat and dominating NMR signal from a tissue component to be suppressed is from water. In this case the main frequency of the system is tuned to fat, and water is treated as the signal that needs to be suppressed, and the values from the above table can be used with opposite signs.

In a third aspect, the invention relates to the use of this embodiment of the method of the first aspect to generate an image with increased contrast for fatty tissues.

In yet another preferred embodiment, the method is directed at silicone gel excitation and water suppression, meaning that a dominating nuclear magnetic resonance (NMR) signal from a tissue component to be excited is from silicone gel and dominating NMR signal from a tissue component to be suppressed is from water. Although silicone gel is not a natural tissue, it is customarily used as a component introduced into tissue in cosmetic surgery. This implies the following values:

| Silicone gel - water | $B_0 = 1.5T$ | $B_0 = 3T$ | $B_0 = 7T$ |
|---|---|---|---|
| $f_e$ | 0 Hz | 0 Hz | 0 Hz |
| $f_s$ | −320 Hz | −640 hz | −1490 Hz |
| $\delta$ | 5.1 ppm | 5.1 ppm | 5.1 ppm |
| $t = 1/(4 \delta B_0 \gamma)$ | 0.8 ms | 0.4 ms | 0.2 ms |

In a fourth aspect, the invention relates to the use of this embodiment of the method of the first aspect to generate an image with increased contrast for silicone gel.

In a fifth aspect, the invention provides a magnetic resonance imaging (MRI) system comprising an MRI apparatus having a plurality of gradient coils positioned about a bore of a magnet to impress a polarizing magnetic field, an RF coil assembly, an RF pulse sequence generator and an RF transceiver system to generate and transmit RF excitation pulses to an RF coil assembly; and a computer programmed to constructing first and second radio-frequency (RF) excitation pulses in accordance with the first aspect of the invention.

With the computer program constructing RF pulses is meant that it sets pulse and inter-pulse parameter values, pulse shape etc. and communicates this to the pulse sequence generator which can then generate the actual RF pulses.

In a sixth aspect, the invention provides a computer for use with an MRI apparatus comprising a computer readable storage medium having thereon a computer program programmed to construct first and second radio-frequency (RF) excitation pulses in accordance with the first aspect of the invention; and transmit the first and second pulses to the pulse sequence generator.

In a seventh aspect, the invention provides a computer program product for constructing excitation pulses for a magnetic resonance imaging (MRI) sequence, the product being adapted to enable a computer system comprising at least one computer having data storage means in connection therewith to construct first and second radio-frequency (RF) excitation pulses in accordance with the first aspect of the invention.

In an eighth aspect, the invention provides a computer program product for updating a magnetic resonance imaging (MRI) system to add excitation pulses that can be created by an RF modulator of the system, the product comprising means for installing software applications which provides the following when executed by a processor:
construct first and second radio-frequency (RF) excitation pulses in accordance with the first aspect of the invention.

The seventh and eighth aspect of the invention relates to a computer program product. Such computer program product is adapted to enable a computer system comprising at least one computer having data storage means associated therewith to control an MRI apparatus or a unit of such to carry out the invention. These aspects of the invention are particularly, but not exclusively, advantageous in that the present invention may be implemented by a computer program product enabling a computer system to perform the operations of the first aspect of the invention. Thus, it is contemplated that some known MRI apparatus, or a unit of such, may be changed to operate according to the present invention by installing a computer program product on a computer system controlling the MRI apparatus. Such a computer program product may be provided on any kind of computer readable medium, e.g. magnetically or optically based medium, or through a computer based network, e.g. the Internet.

The gist of the invention is to provide binomial, off-resonance RF excitation pulses for differentiating tissue excitation that yields a larger fat suppression than prior art water excitation methods. Proper balancing of the frequency offset and the pulse duration with a relative phase offset between the pulses leads to large-bandwidth pass- and stopbands for water and fat, respectively. The pulses can be applied with short, or even zero, interpulse delay, leading to substantial timesavings in the overall imaging sequence.

The individual aspects of the present invention may each be combined with any of the other aspects. These and other aspects of the invention will be apparent from the following description with reference to the described embodiments.

BRIEF DESCRIPTION OF THE FIGURES

The invention will now be described in more detail with regard to the accompanying figures. The figures show one way of implementing the present invention and is not to be construed as being limiting to other possible embodiments falling within the scope of the attached claim set.

FIGS. 8A-8D show MRI images obtained in a phantom using four different MRI methods performed on a cylindrical shaped phantom and a water bottle. The images represent a coronal slice (upper row) and a transversal slice (lower row) within a 3D volume acquired using a 3D GRE acquisition. (FIG. 8A) MRI image obtained without the use of fat suppression techniques, (FIG. 8B) image obtained using conventional fat saturation (FS), (FIG. 8C) image obtained using conventional 1-1 binomial excitation (WE(1-1)), (FIG. 8D) image obtained using off-resonant ($\Delta f=300$ Hz) LIBRE pulses.

DETAILED DESCRIPTION OF AN EMBODIMENT

The first aspect of the invention only specifies the settings of certain RF pulse parameters and application of the resulting pulses, and can thus be implemented on any MRI system with pulse sequence generator capable of generating the first and second pulses and an RF transceiver system and an RF coil assembly capable of transmitting the generated pulses. All standard MRI systems have the required hardware for this implementation.

Figure 1:
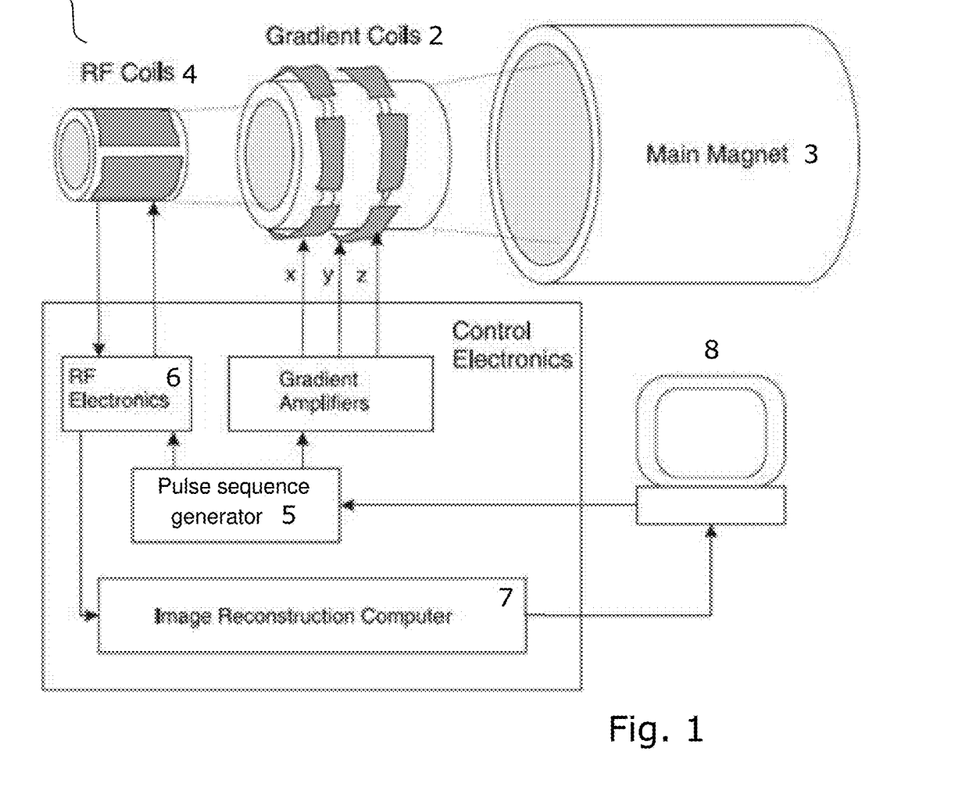
FIG. 1 is a schematic diagram of an MRI system according to an embodiment of the invention.

FIG. 1 illustrates a standard MRI system 1 comprising an MRI apparatus having a plurality of gradient coils 2 positioned about a bore of a main magnet 3 to impress a polarizing magnetic field, an RF coil assembly 4, a pulse sequence generator 5 and an RF transceiver system 6. The system has a computer 8 for constructing the first and second pulses and transmitting them to the generator 5 for generating the first and second RF pulses. The pulse construction involves setting all parameters required by the generator 5 to generate the pulses.

A computer program product used to implement of the seventh aspect of the invention will be described in more detail later. With the computer 8 having a storage medium having such program thereon, the computer 8 can be used to implement the sixth aspect of the invention. Also, the MRI system 1 with such computer can be used to implement the fifth aspect of the invention.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

In the following, for practical purposes, the invention, its aspects, embodiments and features will often be exemplified by reference to the water-fat scenario, where water is the tissue component to be excited and fat is the tissue component to be suppressed. The pulses in this scenario are also referred to as lipid-insensitive off-resonance excitation (LIBRE) pulses. In most cases, these aspects, embodiments and features are equivalently applicable to the fat-water and silicone gel-water scenarios also mentioned previously.

Figure 2:
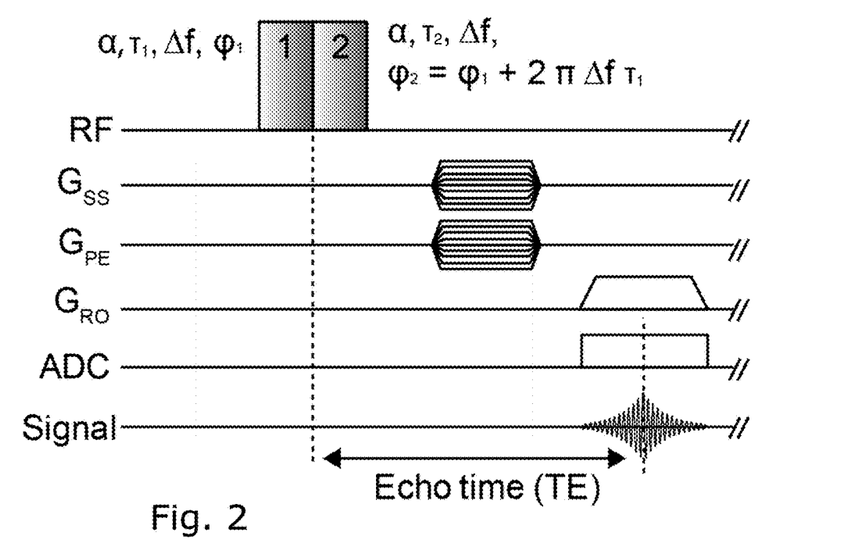
FIG. 2 is a basic MRI pulse sequence diagram illustrating an embodiment of the invention in a 3D GRE MRI sequence with cartesian readout.

FIG. 2 illustrates an example of a 3D GRE MRI sequence with first and second excitation pulses, 1 and 2, according to an embodiment of the invention. Each sub-RF-pulse has the same the same frequency f, duration $\tau_{1/2}$, RF excitation angle $\alpha$, and different phase $\varphi$. Here, the phase offset of the first RF pulse is zero ($\varphi_1=0$), while the relative phase offset of the second RF pulse is determined by the frequency and duration of the first RF pulse, given by $\varphi_2=2\tau\,\Delta f\,\tau_1$.

Besides the MRI sequence that utilizes a gradient recalled echo (GRE) based signal acquisition, the invention can also be combined with the following MRI techniques: ultra short echo time (UTE) techniques, spin echo (SE) or turbo spin echo (TSE) based acquisitions, (balanced) steady state free precession ((b)SSFP) techniques, as well as different trajectories for sampling the data such as spiral, radial or cartesian based patterns. Also, the technique is not limited to imaging of large 3D volumes, but can also be used in targeted volumes.

FRPs

Figure 3B:
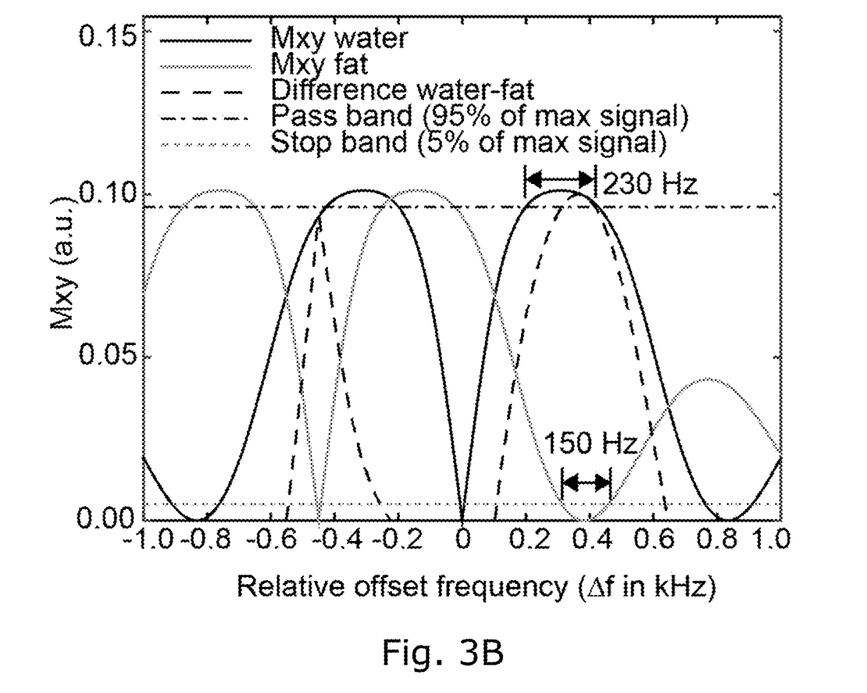

FIGS. 3A and 3B show frequency response profiles (FRP) for water and fat obtained by numerical simulations performed in Matlab (The MathWorks, Inc., Natick, Mass., United States). The simulations were performed to determine the transversal and longitudinal magnetizations and evaluate the FRP of water and fat for the first and second pulses according to an embodiment of the invention, FIG. 3A. These are compared with FRPs from the binomial off-resonant pulse implementation of Ye et al. (2014) and Ye et al. (2015), referred to earlier, in FIG. 3B, which is identical to FIG. 3a of Ye et al. (2014). As can be seen, bandwidths of the pass- and stopbands for the water and fat resonance frequencies are approximately 3.5 and 2.5 times larger for the LIBRE pulses as compared to the BORR pulses.

Ye et al. uses two pulses of which the second pulse has a fixed 180° ($\pi$) phase difference relative to the first pulse, in effective having a RF excitation angles of +$\alpha$ of the first pulse and $-\alpha$ in the second pulse. In the present invention, the phase off-set between the first and the second pulses is not fixed, but a linear function of $\Delta f$ and $\tau$.

Figure 4:
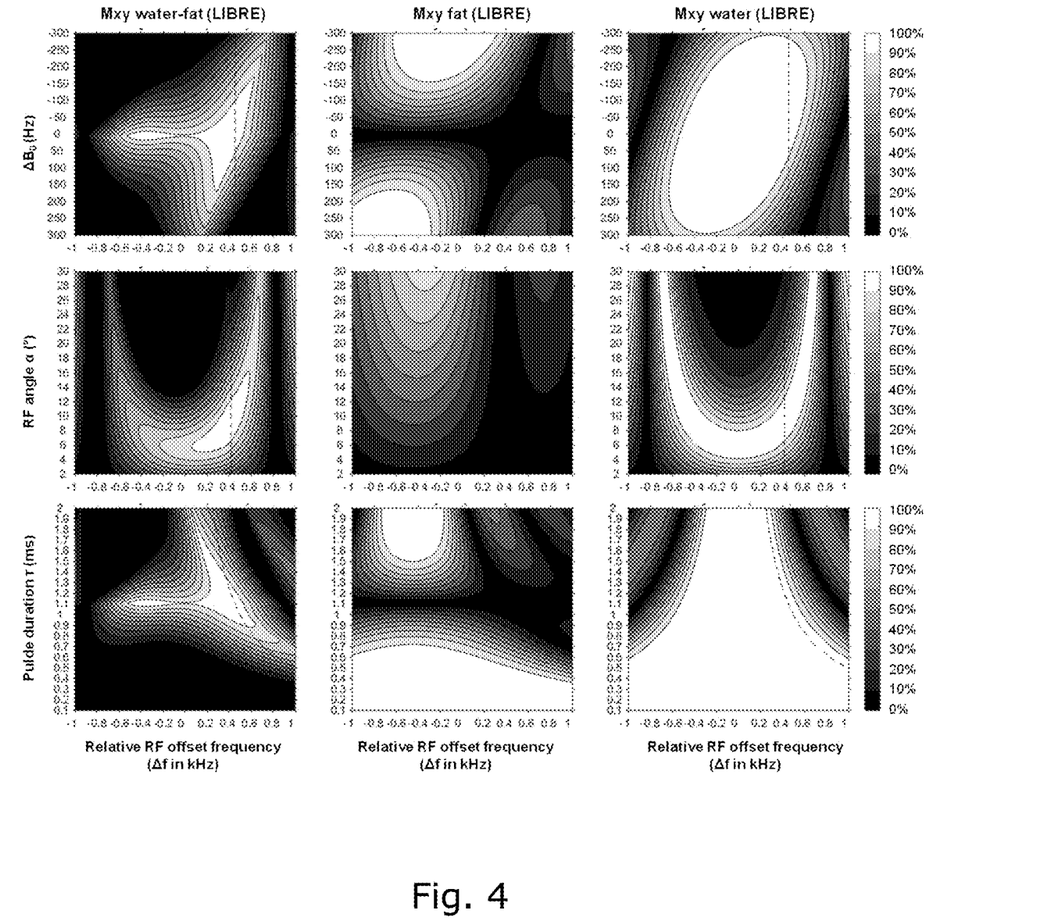
FIG. 4 shows numerical simulations of the signal/magnetization of an embodiment of the invention (LIBRE) for water (right column), fat (middle column), and the difference (left column). These FRPs were determined as function of the magnetic field inhomogeneity (top row), the RF excitation angle (middle row), and the single pulse duration (bottom row). The scale shows percentage of maximum signal.

Numerical simulations were also performed to establish a link between the FRP for the pulses according to an embodiment of the invention and other pulse parameters such as the RF excitation angle, $\alpha$, and the RF pulse duration, $\tau_{1/2}$ (here the same for both pulses). Further, the dependence upon local magnetic field inhomogeneities, $\Delta B_0$, was also explored. FIG. 4 shows the results for the LIBRE pulses for water (right column), fat (middle column), and the difference (left column). The FRP was determined as function of the magnetic field inhomogeneity (top row), the RF excitation angle (middle row), and the pulse duration (bottom row). More detailed comments to these FRP will follow later.

Figure 5A:
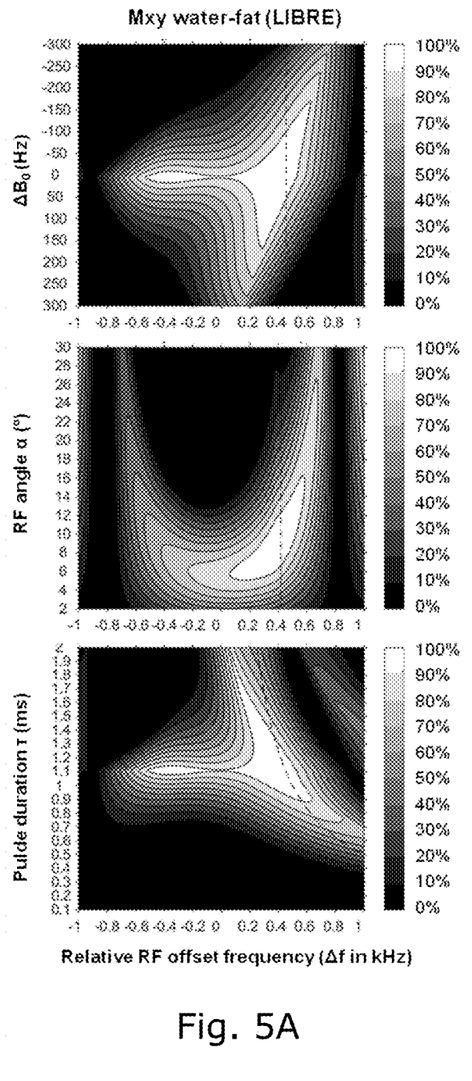
FIGS. 5A and 5B compare the FRPs of the left column of FIG. 4 (FIG. 5A, LIBRE) with a prior art implementation of a binomial pulse (FIG. 5B, Ye et al. (2014); Ye et al. (2015)). The FRP was determined as function of the magnetic field inhomogeneity (top row), the RF excitation angle (middle row), and the single pulse duration (bottom row).
Figure 5B:
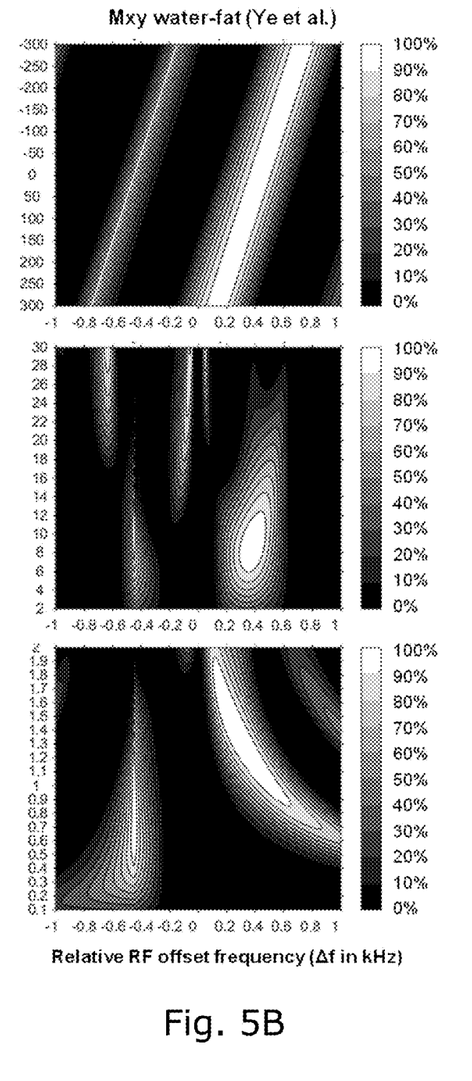

FIGS. 5A and 5B compare the FRPs of the left column of FIG. 4 (FIG. 5A, LIBRE) with the prior art implementation of a binomial pulse from Ye et al. (2014) and Ye et al. (2015) (FIG. 5B). The FRPs was determined as function of the magnetic field inhomogeneity (top row), the RF excitation angle (middle row), and the pulse duration (bottom row).

Next some general comments to each pulse parameter as well as the excitement objectives is given and thereafter the selection of pulse parameter values based on numerical simulation is demonstrated.

Frequency Offset, $\Delta f$

The frequency of the excitation pulses, f, are off-resonance to bulk protons in the tissue components to be excited, $f_e$. The magnetic resonance frequencies of protons generally depend on the magnetic field strength and the chemical configuration of the protons. The following table shows the relative resonance frequencies of bulk protons in some substances for typical magnetic field strengths:

| $f_{res}$ | $B_0 = 1.5T$ | $B_0 = 3T$ | $B_0 = 7T$ |
| --- | --- | --- | --- |
| Water | 0 Hz | 0 Hz | 0 Hz |
| Fat/lipids | 220 Hz | 440 Hz | 1030 Hz |
| Silicone gel | 320 Hz | 640 Hz | 1490 Hz |

The frequency off-set, $\Delta f = f - f_e$, is selected so that f lies on the opposite side of $f_e$ from a resonance frequency of protons to be suppressed, $f_s$, in the frequency spectrum, i.e. in a direction away from $f_s$. For example, to suppress fat and image water, we move away from the fat, i.e. if water is 0 Hz, fat is −440 Hz, and $\Delta f$ can be at around 200-500 Hz. To suppress water and image fat instead one could change the main frequency to fat and change the frequency offset of pulse to −200-−500 Hz.

The frequency off-set is closely tied to the pulse shape and duration through Fourier Transform analysis. With preferred pulse shapes giving rise to a sinc-like shapes in the frequency domain, in which the positions of peaks and troughs (zero-crossings) depends on both the (carrier) frequency of the pulse (f) and the duration of the pulse. The positions of peaks and troughs in the frequency spectrum again influences the position and bandwidth of the pass- and stopbands in the FRPs of the tissue components.

Pulse Duration, $\tau$

The pulse durations of the first and second pulses do generally not differ much from known WE binomial 1-1 pulse, but is not so fixed as the ones from a known WE binomial 1-1 pulse. As the simulations show, the pulse duration in the present invention is more flexible and can be chosen within a range of values.

As mentioned previously, the pulse duration and frequency off-set is closely related. Generally, a shorter pulse duration can be used if the carrier frequency goes further off-resonance, e.g. from $\Delta f = 400$ Hz to $\Delta f = 800$ Hz. This is possible because the pulse becomes less sensitive to fat when applied further off-resonance. In other words, if the pulse becomes shorter, the zero crossings of the sinc-shaped frequency response are more widely spaced, and to align those with the fat resonance frequency the offset moves further off-resonance. The following table shows example values of $\Delta f$ and total pulse duration $\tau$ for different magnetic field strengths as have been applied in some numerical simulations.

| Water - fat | $B_0 = 1.5T$ | $B_0 = 3T$ | $B_0 = 7T$ |
| --- | --- | --- | --- |
| $f_e$ | 0 Hz | 0 Hz | 0 Hz |
| $f_s$ | −220 Hz | −440 Hz | −1030 Hz |
| $\Delta f$ | 200 Hz | 400 Hz | 800 Hz |
| $\tau$ (max) | 4.5 ms | 2.3 ms | 1.0 ms |

In MRI, it is typically of interest to decrease the measurement to save time and costs. Hence, a shorter excitation pulse duration would be advantageous. Looking at the water-fat FRP for the pulse duration (lower left corner of FIG. 4), an acceptable signal different of 80% can be retained when $\tau_{1,2} = 0.6$-$0.9$ ms (corresponding to a total RF duration of $\tau = 1.2$-$1.8$ ms).

The black regions in the bottom center panel of FIG. 4 shows a range of single pulse durations and RF offset frequencies at which the fat signal is suppressed. This optimal region ranges from a single pulse duration of 2 ms and a RF offset of 0 Hz towards and beyond a single pulse duration of 0.7 ms with an RF offset of 1000 Hz. Intuitively speaking, the parameter combinations in this region generates a full rotation of fat around the effective RF field. In addition this region coincides with a parameter range of optimal water excitation (bright region bottom right panel, FIG. 4), and is emphasized in the bottom left panel of FIG. 4, where the subtraction of both signals is shown. A very broad fat suppression is obtained as can be seen in the fat FRP for the pulse duration (lower centre) in FIG. 4. For a single pulse duration of 1.1 ms, fat is almost everywhere suppressed irrespective of the offset frequency.

Relative Phase Offset

It is important to distinguish between prior art pulses with a phase shift of $\pi$ (as in the Ye et al. papers) and pulses according to the invention where $\Delta\varphi = 2\pi\, \Delta f\, \tau_1 = \pi$. It is not sufficient for a prior art excitation pulse pair to accidentally have the same $\Delta\varphi$ as a set of LIBRE pulses, if $\Delta f$ and $\tau_1$ of the first pulse in the pair are not related to this phase shift via $\Delta\varphi = 2\pi\, \Delta f\, \tau_1$ (as described previously, the invention still produces applicable results as long as $\Delta\varphi$ falls within 10%, 5% or 3% of this expression—this is implicit in the following discussions of $\Delta\varphi$). As stressed previously, the FRPs depends on the relation between several pulse parameters, not just on the value of the phase shift. In FIGS. 4 and 5A, the dashed black line in the FRPs indicates the combinations of parameter values for the first and second pulses where the phase difference is $\Delta\varphi = 2\pi\, \Delta f\, \tau_1 = \pi$.

There are important differences between:

$\Delta\varphi = \pi = 2\pi\, \Delta f\, \tau_1$ for pulses in accordance with the present invention, and $\Delta\varphi = \pi \neq 2\pi\, \Delta f\, \tau_1$ for the pulses applied in the Ye et al. papers.

For pulses in accordance with the invention, as can be seen from the simulations shown in FIGS. 4 and 5A and 5B, the behavior of the FRP is different with respect to $B_0$ inhomogeneities and RF angle (B1 inhomogeneities), and the optimal pulse duration is dramatically different.

It also appears that it is the water signal which is correlated with the $\Delta\varphi=\tau=2\pi\,\Delta f\,\tau_1$ line and not that of fat. The fat suppression does not seem to be related to this condition, and depends more on the pulse duration, as described in the previous section—for $\tau_1=1.1$ ms, fat is suppressed irrespective of the frequency. However, the fat suppression of the Ye et al pulses does not show this dependency on the pulse duration, and has no broad passband for $\tau_1=1.1$ ms, see FIG. 5B.

In a preferred embodiment of all aspects of the invention, the case $\Delta\varphi\neq\pi$ is explicitly disclaimed in that values of $\Delta f$ and $\tau_1$ are selected so that $2\,\Delta f\,\tau_1\neq I$, where I is an integer. This serves to avoid accidental disclosures of parameter values in accordance with the invention.

Another practical advantage of the pulses in accordance with the invention are that their implementation allows the exact same (transmitter) phase offset in the center of each pulse (pulse 1 and pulse 2) as well as the (receiver) phase offset during acquisition. The phase offset of both transmitter and receiver changes in the same fashion with each acquisition (called phase cycling). This feature of the pulse is only possible because in the LIBRE implementation the phase evolution of the transmitter is exactly the same in each pulse, which results in exactly the same phase offset in the center of each pulse, and allows the same phase of the signal receiver. Although this cannot be experimentally verified at present, it might be another beneficial aspect of the LIBRE pulse that contributes to enhanced fat suppression.

Interpulse Delay, t

Typical WE binomial 1-1 pulses consist of two short pulses with a interpulse delay corresponding to 180° phase evolution between water and fat protons, this is 1.1 ms at 3 T. This is important in order to turn the fat magnetization back to alignment with $B_0$ while keeping the water magnetization excited.

The present invention allows for a smaller or even zero interpulse delay, which can significantly reduce imaging sequence durations.

RF Excitation Angle

The Excitation pulses according to the invention can have higher RF excitation angles than prior art excitation pulses. Firstly, the relatively long pulse duration allows for the use of lower RF power for identical RF excitation angles as it is defined by the pulse duration times its amplitude. The RF energy (~Amplitude$^2$) deposit in the tissue is thus significantly lower in pulses of similar angle but are of longer duration with less amplitude. Since the RF energy deposit is often limited and fixed on MRI systems for safety reasons, using lower power pulses might contribute to less RF energy deposit, and shortens scan time. Secondly, the simulations show that there is a larger range of optimal RF excitation angles. Even if the RF energy deposit in tissues is not everywhere equal, this range of optimal RF excitation angles indicates that the method according to the invention is less sensitive to B1 inhomogeneities.

Magnetic Field Inhomogeneities

In practice in MRI there are small magnetic field inhomogeneities that vary across different spatial locations and which cause the Larmor frequency and all values related to vary across the body. It is therefore important that methods to be implemented are insensitive to such inhomogeneities in order to give consistent results.

Depending on the type of imaging and the volume to be imaged, the sensitivity towards magnetic field inhomogeneities can go from essential to of less importance. Low sensitivity to inhomogeneities is therefore a relevant objective when designing (i.e. selecting parameters for) pulses in MRI sequences.

As can be seen from the upper row of FIG. 4, the response of water-fat for the LIBRE pulses has a low sensitivity towards small variations in $\Delta B_0$ (inhomogeneities) for $\Delta f$ in the interval 100-600 Hz.

Pass- and Stopband Bandwidth

Due to the local changes in magnetic field strength there are changes in the resonance frequency of tissues. It could thus be that a certain tissue type resonates at a small range of frequencies and therefore it is desirable to have a certain level of pass band and stopband so that it is effectively targeting a range of frequencies.

Selection of Pulse Parameters

Designing pulses for differentiating tissue excitation in accordance with the invention involves selecting values for a number of pulse and inter-pulse parameters. According to an embodiment of the invention, such parameter values can be selected by performing a numerical simulation of the excitation and suppression of bulk protons in the tissue components with the parameter to be selected as a variable. The results could look like the FRPs presented in FIGS. 4-6B. The result of the simulation shows which parameter values would give which excitation and suppression, and there will often be a value giving the maximum effect.

Since, the effective excitation and suppression depends on many parameters and since the parameters are interrelated, it is typically not possible to simply choose the values with maximum effect for all parameters. Therefore, the choice of parameter values often depends on the purpose of the imaging, which can be reduced to the objective with applying the differentiated tissue excitation. As an example, for some parameters, values are chosen that may not give the largest fat suppression, but instead gives a suppression that is less sensitive to magnetic field inhomogeneities. Therefore, after the simulation, values for the parameters can be selected from the result of the simulation under one or more objectives of the differentiated tissue excitation.

Several such objectives are described in the previous sections, and more can be found and developed.

Silicone Gel-Water

Figure 6A:
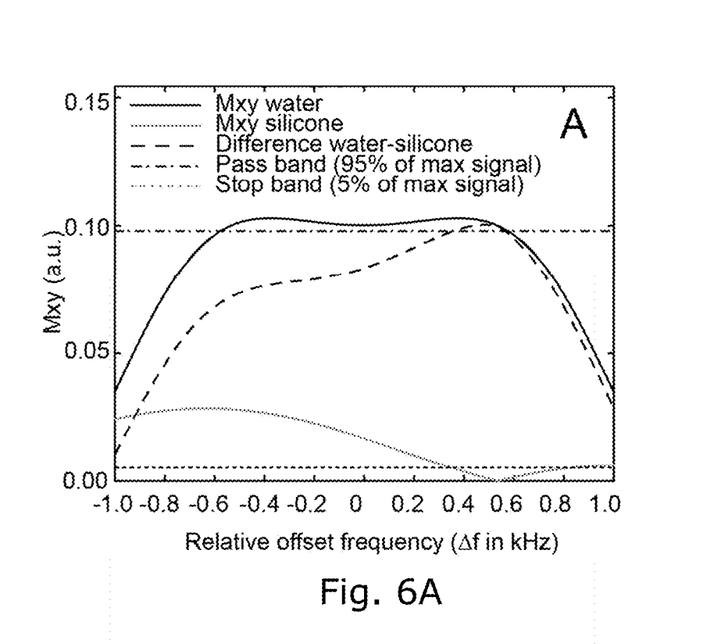
FIGS. 6A and 6B show numerical simulations on a silicon gel-water system of the FRP of an embodiment of the invention (FIG. 6A, LIBRE) and of a prior art implementation of a binomial pulse (FIG. 6B, Ye et al. (2014)).
Figure 6B:
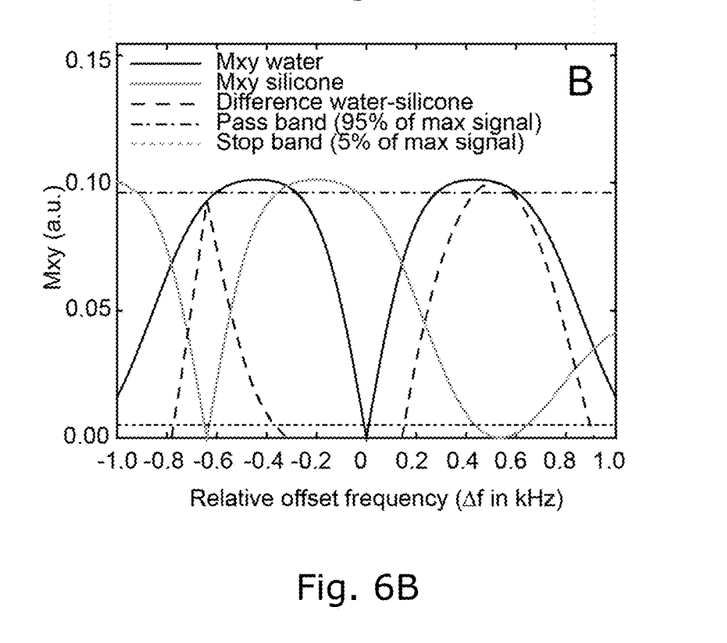

The invention can be applied to enhance and/or suppress excitation in different systems than water and fat. FIGS. 6A and 6B show numerical simulations on a silicon gel-water system of the FRP of an embodiment of the invention (FIG. 6A, LIBRE) and of a prior art implementation of a binomial pulse (FIG. 6B, Ye et al. (2014)). This excitation pulse sequence can be used to generate an image with increased contrast for silicone gel, which may be helpful when looking for leakage in cosmetic chirurgic implants.

Fat-Water

Similarly, it may be of interest to enhance the excitation of fat and suppress water. This can be used to generate an image with increased contrast for fat, which may be helpful when assessing body fat indices or quantizing obesity.

Experimental Results (Phantoms)

Figure 7A:
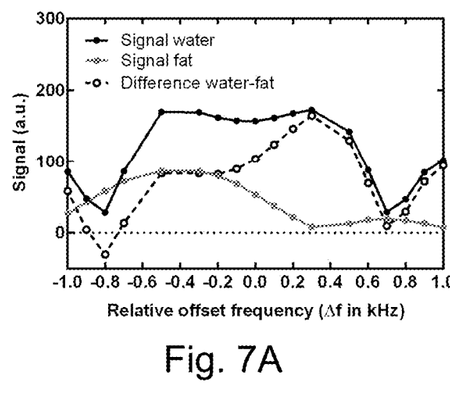
FIGS. 7A and 7B show the difference in signals between water and fat obtained in a phantom as function of (FIG. 7A) frequency offset ($\Delta f$) and (FIG. 7B) single pulse duration ($\tau_1$). Note that these results match the numerical simulations in FIG. 3.
Figure 7B:
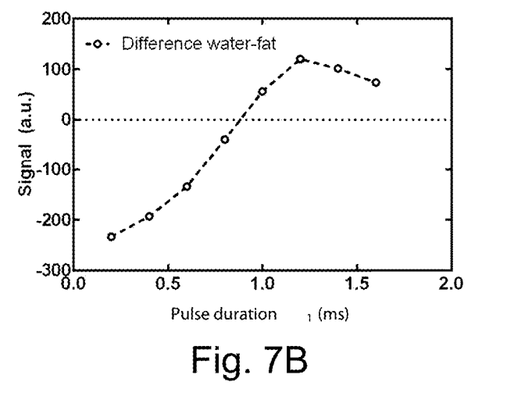
Figure 8A:
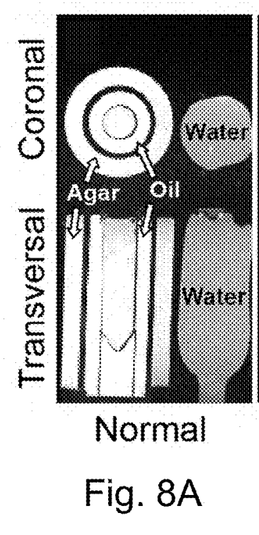
Figure 8B:
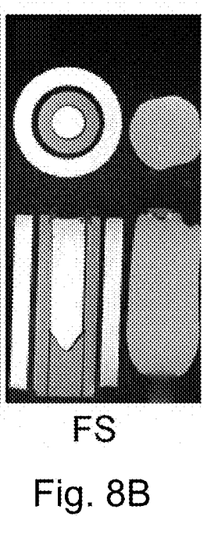
Figure 8C:
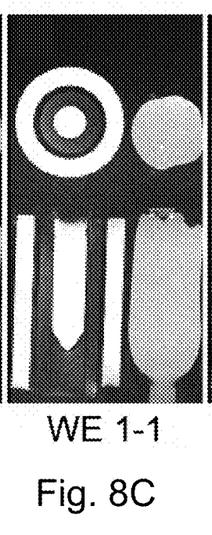
Figure 8D:
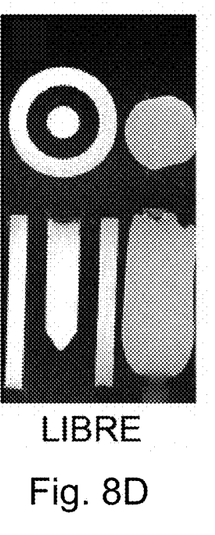

This section describes some experimental tests using phantoms. FIGS. 7A and 7B show the difference in signals between water and fat obtained in a phantom as function of (FIG. 7A) frequency offset ($\Delta f$) and (FIG. 7B) single pulse duration ($\tau_1$). Signal differences are obtained in a phantom containing baby oil and water. From MRI images the signals were calculated and plotted as function of the frequency offset of the LIBRE pulse. It shows a certain region (200-400 Hz) where the fat suppression is optimal. FIG. 7B shows the signal difference of water and fat as function of the duration of the LIBRE pulse. It also shows that there is a certain pulse duration that fat suppression is maximized, and contrast between water and fat is maximized.

FIGS. 8A-8D show MRI images obtained in a phantom using four different MRI methods performed on a cylindrical shaped phantom and a water bottle. The images represent a coronal slice (upper row) and a transversal slice (lower row) within a 3D volume acquired using a 3D GRE acquisition. The central compartment of the cylindrical phantom contains agar, the middle compartment baby oil and the outer compartment contains agar. (FIG. 8A) MRI image obtained without the use of fat suppression techniques, (FIG. 8B) image obtained using conventional fat saturation (FS), (FIG. 8C) image obtained using conventional 1-1 binomial excitation (WE(1-1)), (FIG. 8D) image obtained using off-resonant ($\Delta f$=300 Hz) LIBRE pulses.

It is shown that the LIBRE pulses results in a visibly better fat suppression that the other methods.

Figure 9:
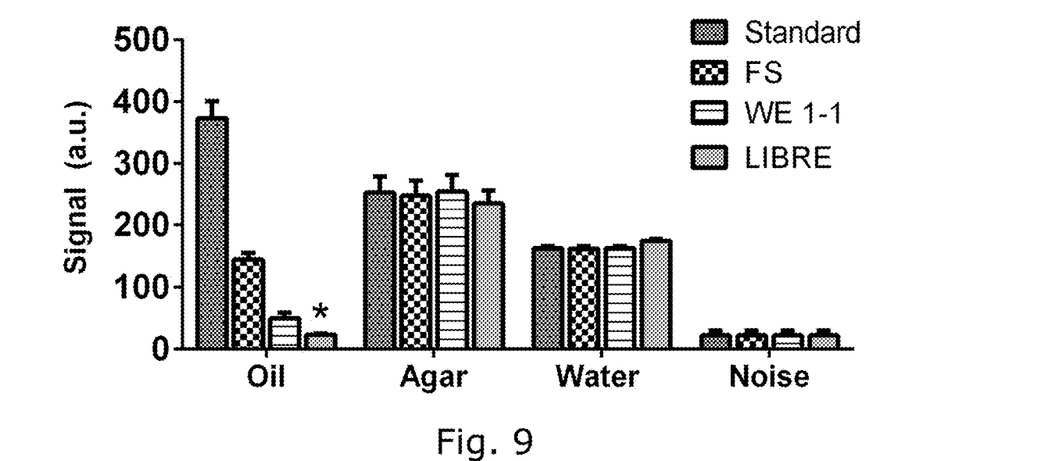
FIG. 9 show the average signals measured in regions of interests (ROIs) drawn in water, agar, fat and noise compartments in MRI images shown in FIGS. 8A-8D. Using LIBRE there is a significant decrease (P<0.05) of the fat signal compared with the other techniques, effectively reducing the fat signal to noise levels.

FIG. 9 shows average signals measured in regions-of-interests (ROIs) drawn in water and fat compartments in MRI images shown in FIGS. 8A-8D, and Contrast-to-noise ratio (CNR) between the water and oil compartments. Error bars represent ±standard deviation of the average signal in the ROIs.

EXPERIMENTAL RESULTS (IN VIVO)

Figure 10:
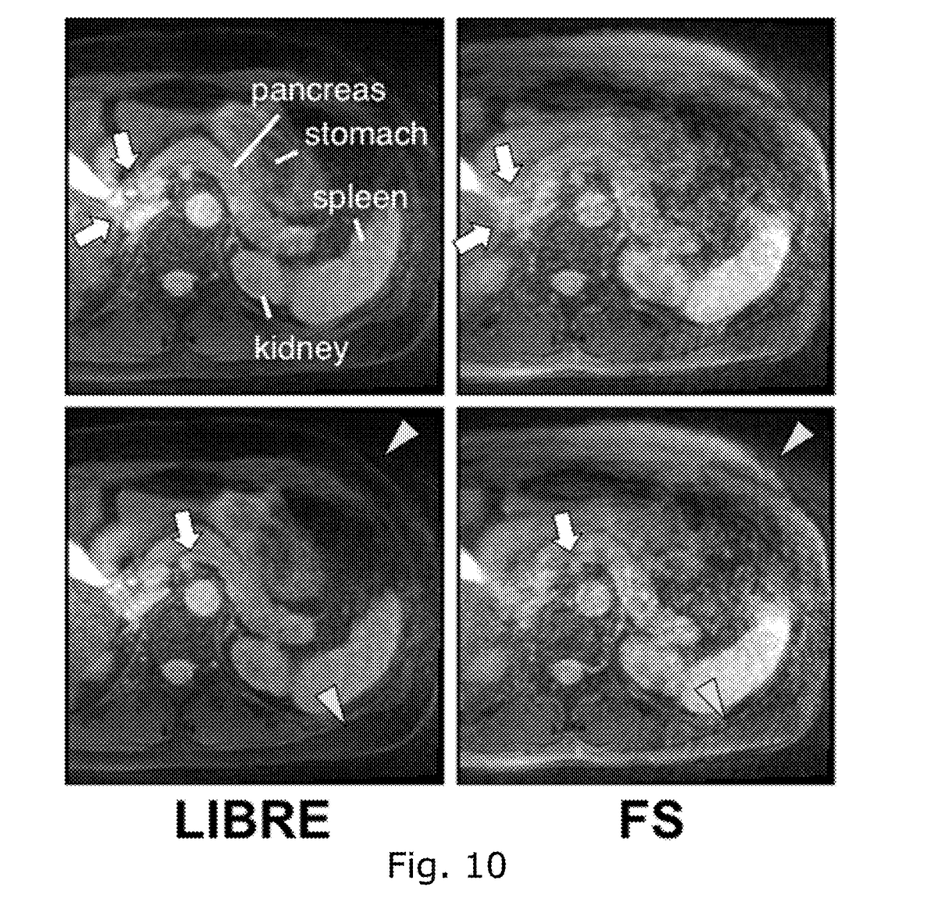
FIG. 10 shows MRI images of the abdominal region showing several organs such as the pancreas, liver, kidneys obtained with conventional fat saturation (FS) and the LIBRE pulses.

FIG. 10 shows MRI images obtained at 3 T in healthy volunteers of the abdominal region showing several organs such as the pancreas, liver, kidneys. A comparison is made between a conventional fat saturation (FS) pulse and the use of the invention (LIBRE). Note the enhanced and uniform fat suppression of subcutaneous fat as well as between the organs (arrows).

The invention claimed is:

1. A method for differentiating tissue excitation in magnetic resonance imaging (MRI), comprising applying during an image acquisition sequence of an MRI system first and second radio-frequency (RF) excitation pulses, where the first and second pulses are off-resonance to protons in a tissue component to be excited by having a central frequency, f, offset from a central resonance frequency of protons in the tissue component to be excited, $f_e$, by a predetermined frequency offset, $\Delta f$, in a direction away from a central resonance frequency of protons in a tissue component to be suppressed, $f_s$, where the first and second pulses have the same RF excitation angle, $\alpha$, and respective phases, $\varphi_1$ and $\varphi_2$, characterized in that:
a phase shift between the pulses is related to the frequency offset, $\Delta f$, and a pulse duration of the first pulse, $\tau_1$, by:

$\varphi_1=\varphi_0; \varphi_2=\varphi_0+r2\pi\Delta f\tau_1$ with r being a number in the interval [0.9; 1.1] and $2\Delta f\tau_1 \neq I$, where I is an integer, resulting in a pulse sequence having a passband including $f_e$ in a frequency response profile for the protons in the tissue component to be excited and a stopband including $f_s$ in a frequency response profile for the protons in the tissue component to be suppressed; and
any interpulse delay, t, between the end of the first pulse and the beginning of the second pulse is smaller than a time for 90° phase evolution between the protons in the respective tissue components:

$t<1/(4\ \delta B_0\gamma)$, where $\delta$ is the chemical shift between the protons in tissue to be excited and suppressed, $\delta=(f_s-f_e)/f_e$, $B_0$ is the magnetic field strength, and $\gamma$ is the gyromagnetic ratio of the nucleus; and generating an image based on the applied sequence.

2. The method according to claim 1, wherein the first and second pulses have the same pulse duration $\tau_2=\tau_1$.

3. The method according to claim 1, wherein each of the first and the second pulses has a duration, $\tau_{1,2}$, in the interval 0.6-0.9 ms.

4. The method according to claim 1, wherein a total pulse duration of the first and second pulses, $\tau=\tau_1+\tau_2$, is in the interval 1.2-1.8 ms.

5. The method according to claim 1, wherein the first and second RF pulses are rectangular pulses.

6. The method according to claim 1, further comprising selecting a value of at least one parameter from the group consisting of pulse shape, pulse amplitude, $\Delta f$, $\tau_1$, $\alpha$, $\varphi_0$, $f_e$, $f_s$, $B_0$, and t by performing a numerical simulation of excitation and suppression of bulk protons in the tissue components with at least the selected parameter as a variable; and selecting a value of the selected parameter from the result of the simulation under an objective of the differentiated tissue excitation.

7. The method according to claim 1, wherein the method is directed at water excitation and fat suppression, so that the tissue component to be excited is water and the tissue component to be suppressed is fat.

8. The method according to claim 7, wherein the image is an MR image and MR signals originating from fat are reduced image.

9. The method according to claim 1, wherein the image has increased contrast for fatty tissues, wherein the tissue component to be excited is fat and the tissue component to be suppressed is water.

10. The method according to claim 1, wherein the image has increased contrast for silicone gel, wherein the tissue component to be excited is silicone gel and the tissue component to be suppressed is water.

11. A magnetic resonance imaging (MRI) system comprising an MRI apparatus having a plurality of gradient coils positioned about a bore of a magnet to impress a polarizing magnetic field, an RF coil assembly, an RF pulse sequence generator and an RF transceiver system to generate and transmit RF excitation pulses to the RF coil assembly; and
a computer programmed to construct first and second radio-frequency (RF) excitation pulses and transmit the constructed first and second pulses to the RF pulse sequence generator, where the first and second pulses are off-resonance to protons in a tissue component to be excited by having a central frequency, f, offset from a central resonance frequency of the protons in the tissue component to be excited, $f_e$, by a predetermined frequency offset, $\Delta f$, in a direction away from a central resonance frequency of protons in a tissue component to be suppressed, $f_s$, where the first and second pulses have the same RF excitation angle, $\alpha$, and respective phases, $\varphi_1$ and $\varphi_2$, characterized in that:
a phase shift between the pulses is related to the frequency offset, $\Delta f$, and a pulse duration of the first pulse, $\tau_1$, by:

$\varphi_1=\varphi_0; \varphi_2=\varphi_0+r2\pi\Delta f\tau_1$ with r being a number in the interval [0.9; 1.1] and $2\Delta f\tau_1 \neq I$, where I is an integer, resulting in a pulse sequence having a passband including $f_e$ in a frequency response profile for the protons in the tissue component to be excited and a stopband including $f_s$ in a frequency response profile for the protons in the tissue component to be suppressed; and any interpulse delay, t, between the end of the first pulse and the beginning of the second pulse is smaller than a time for 90° phase evolution between the protons in the respective tissue components:

$$t<1/(4\delta B_0\gamma),$$

where $\delta$ is the chemical shift between the protons in tissue to be excited and suppressed, $\delta=(f_s-f_e)/f_e$, $B_0$ is the magnetic field strength, and $\gamma$ is the gyromagnetic ratio of the nucleus; and generating an image based on the constructed pulses.

12. A computer program product for constructing excitation pulses for a magnetic resonance imaging (MRI) sequence, the product comprising a non-transitory computer readable storage medium having computer readable software applications embodied in the medium which provides the following when executed by a processor:

constructing first and second radio-frequency (RF) excitation pulses, where the first and second pulses are off-resonance to protons in a tissue component to be excited by having a central frequency, f, offset from a central resonance frequency of the protons in the tissue component to be excited, $f_e$, by a predetermined frequency offset, $\Delta f$, in a direction away from a central resonance frequency of protons in a tissue component to be suppressed, $f_s$, where the first and second pulses have the same RF excitation angle, $\alpha$, and respective phases, $\varphi_1$ and $\varphi_2$, characterized in that:

a phase shift between the pulses is related to the frequency offset, $\Delta f$, and a pulse duration of the first pulse, $\tau_1$, by:

$$\varphi_1=\varphi_0; \varphi_2=\varphi_0+r2\pi\Delta f\tau_1$$

with r being a number in the interval [0.9; 1.1] and 2 $\Delta f$ $\tau_1 \neq I$, where I is an integer, resulting in a pulse sequence having a passband including $f_e$ in a frequency response profile for the protons in the tissue component to be excited and a stopband including $f_s$ in a frequency response profile for the protons in the tissue component to be suppressed; and any interpulse delay, t, between the end of the first pulse and the beginning of the second pulse is smaller than a time for 90° phase evolution between the protons in the respective tissue components:

$$t<1/(4\delta B_0\gamma),$$

where $\delta$ is the chemical shift between the protons in tissue to be excited and suppressed, $\delta=(f_s-f_e)/f_e$, $B_0$ is the magnetic field strength, and $\gamma$ is the gyromagnetic ratio of the nucleus; and generating an image based on the constructed pulses.

* * * * *